United States Patent [19]

Paradissis et al.

[11] Patent Number: 5,296,232
[45] Date of Patent: * Mar. 22, 1994

[54] PHARMACEUTICAL FORMULATION WHICH DOES NOT INDUCE TOLERANCE

[75] Inventors: George N. Paradissis, St. Louis; James A. Garegnani, Ballwin; Roy S. Whaley, St. Louis, all of Mo.

[73] Assignee: KV Pharmaceutical Company, St. Louis, Mo.

[*] Notice: The portion of the term of this patent subsequent to Jun. 16, 2009 has been disclaimed.

[21] Appl. No.: 882,537

[22] Filed: May 13, 1992

Related U.S. Application Data

[63] Continuation of Ser. No. 349,533, May 5, 1989, Pat. No. 5,122,384.

[51] Int. Cl.$^5$ .......................... A61K 9/52; A61K 9/22
[52] U.S. Cl. ...................... 424/451; 424/456; 424/458; 424/459; 424/460; 424/461; 424/462; 424/463
[58] Field of Search ............. 424/451, 456, 458, 459, 424/460, 461, 462, 463

[56] References Cited

U.S. PATENT DOCUMENTS

| | | | |
|---|---|---|---|
| 3,623,997 | 11/1971 | Powell | 252/316 |
| 4,000,254 | 12/1976 | Gordon et al. | 424/23 |
| 4,083,949 | 4/1978 | Benedikt | 424/19 |
| 4,173,626 | 11/1979 | Dempski et al. | 424/19 |
| 4,252,786 | 2/1981 | Weiss et al. | 424/19 |
| 4,503,031 | 3/1985 | Glassmann | 242/15 |
| 4,592,753 | 6/1986 | Panoz | 604/897 |
| 4,609,542 | 9/1986 | Panoz et al. | 424/19 |
| 4,610,870 | 9/1986 | Jain et al. | 424/19 |
| 4,611,008 | 9/1986 | Heinzelmann | 514/470 |
| 4,634,587 | 1/1987 | Hsiao | 424/19 |
| 4,666,703 | 5/1987 | Kopf | 424/470 |
| 4,695,467 | 9/1987 | Uemura et al. | 424/502 |
| 4,716,040 | 12/1987 | Panoz | 424/459 |
| 4,721,619 | 1/1988 | Panoz et al. | 424/459 |
| 4,800,084 | 1/1989 | Zerbe | 424/458 |
| 4,826,688 | 5/1989 | Panoz et al. | 424/458 |
| 4,891,230 | 1/1990 | Geoghegan et al. | 424/461 |
| 4,963,365 | 10/1990 | Samejima et al. | 424/46 |

FOREIGN PATENT DOCUMENTS

| | | |
|---|---|---|
| 763735 | 3/1971 | Belgium . |
| 1183665 | 3/1985 | Canada . |
| 0103991 | 3/1984 | European Pat. Off. . |
| 0122077 | 10/1984 | European Pat. Off. . |
| 325843-A2 | 2/1989 | European Pat. Off. . |
| 55-045601 | 3/1980 | Japan . |
| 86/01717 | 3/1986 | PCT Int'l Appl. . |
| 1182124 | 2/1970 | United Kingdom . |
| 1245467 | 9/1971 | United Kingdom . |
| 2098867A | 12/1982 | United Kingdom . |
| 2141342A | 12/1984 | United Kingdom . |
| 2159715A | 12/1985 | United Kingdom . |

OTHER PUBLICATIONS

A Copy of the Dow Chemical Company article, "Formulating for Controlled Release with METHOCEL TM Cellulose Ethers."
*The United States Pharmacopeia*, Twenty-First Revision, pp. 1243-1244.

*Primary Examiner*—Thurman K. Page
*Assistant Examiner*—Robert H. Harrison
*Attorney, Agent, or Firm*—Nath, Amberly & Associates

[57] ABSTRACT

A controlled-release organic nitrate formulation for once-per-day oral administration is provided by spheres having a core which includes an organic nitrate, and a membrane surrounding the core composed of a pharmaceutically acceptable, film forming polymer. The film forming polymer is effective to permit release of the organic nitrate from the spheres, over a daily dosing period, at a rate that achieves a therapeutically effective level of the organic nitrate, while effecting a drug holiday towards a latter portion of the daily dosing period so as not to induce tolerance.

16 Claims, 2 Drawing Sheets

KV CONTROLLED-RELEASE NITROGLYCERIN
EFFECT ON TIME TO ONSET OF CHEST PAIN
AFTER 28 DAYS OF DOSING

MEANS OF 20 PATIENTS
COMBINED KV DOSES COMPARED WITH PLACEBO
DEMONSTRATING LACK OF TOLERANCE

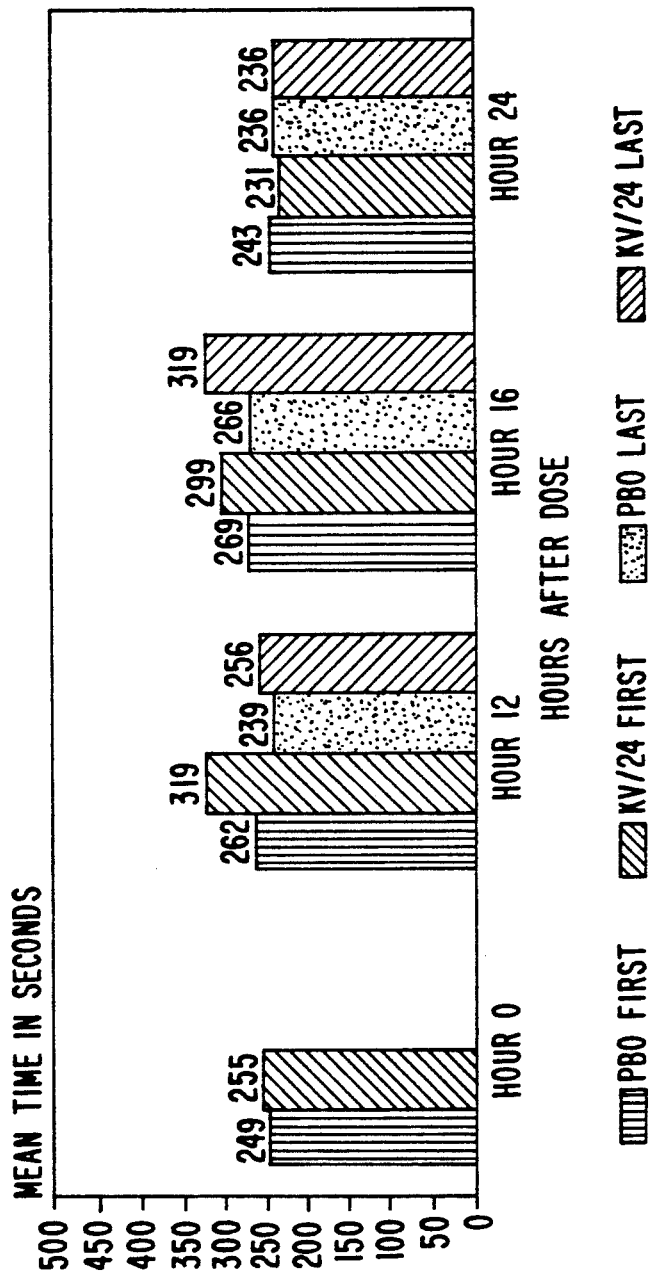

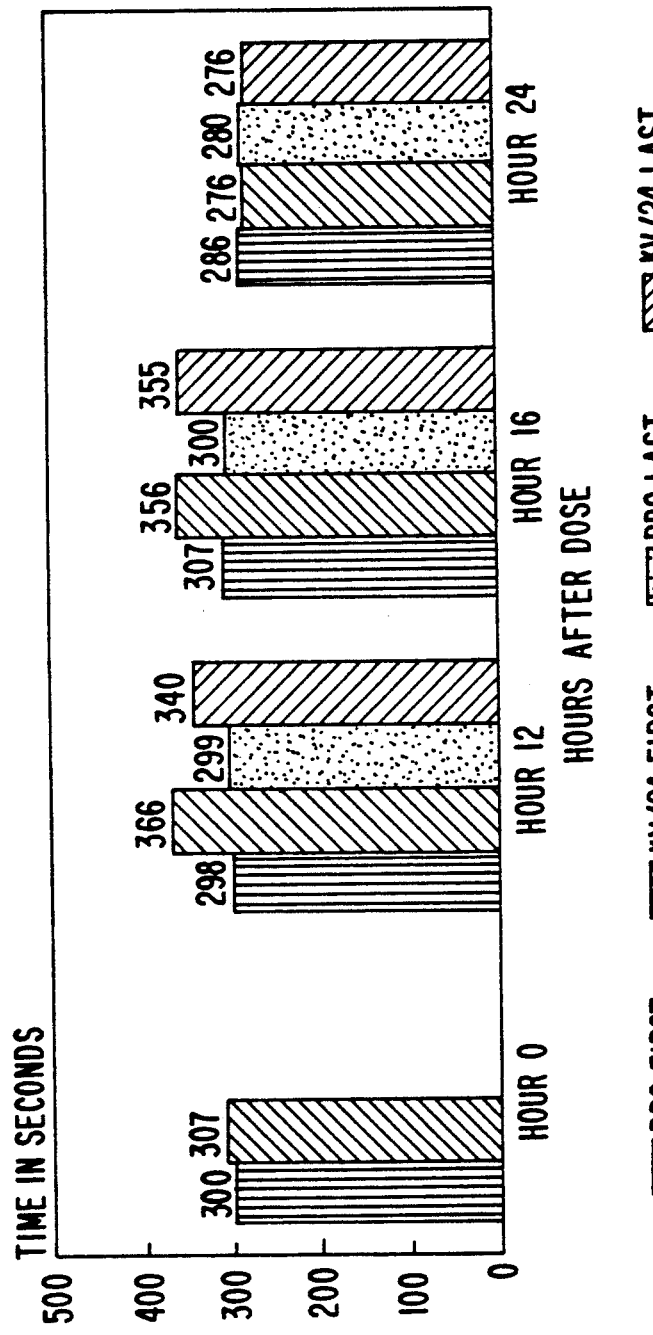

PHARMACEUTICAL FORMULATION WHICH DOES NOT INDUCE TOLERANCE

RELATED APPLICATIONS

This is a continuation application of U.S. application Ser. No. 07/349,533 field May 5, 1989, entitled "ORAL ONCE-PER-DAY ORGANIC NITRATE FORMULATION WHICH DOES NOT INDUCE TOLERANCE", now issued as U.S. Pat. No. 5,122,384.

BACKGROUND OF THE INVENTION

1. Field of the Invention

The present invention relates to controlled-release organic nitrate formulations for oral administration. More particularly, the present invention is directed to nonpareils or sugar spheres coated with an organic nitrate triturate mixed with or without a carrier, a seal coat, and a polymeric membrane as means for controlling the diffusion and release of the organic nitrate. The present invention is also directed to administering the formulation to patients once per day so as to delay or prevent the onset of chest pain for at least sixteen hours after the dose without inducing pharmacologic tolerance to the drug.

2. Discussion of Background and Material Information

Organic nitrates have been used for over a century by physicians for the treatment of cardiovascular disease. Organic nitrates function as relaxants of smooth muscle and especially as dilators of blood vessels. As such, they are used in the treatment of angina pectoris, in which dilation of the coronary vasculature improves myocardial blood flow and oxygen delivery. A second mechanism of action in angina is the reduction of peripheral resistance due to relaxation of veins and arterioles, reducing cardiac workload and, therefore, myocardial oxygen demand. In the treatment of congestive heart failure, dilation of the pulmonary vasculature results in increased blood return to the heart and decreased cardiac preload and afterload, leading to improved cardiac output.

Nitroglycerin, which has been the traditional mainstay in the acute treatment of angina, is well-absorbed from the gastrointestinal tract, but has an extremely short plasma half-life due to extensive first-pass metabolism. These pharmacokinetics have led to the use of nitroglycerin as a short-acting nitrate. In this sense, and because of its low vapor pressure, nitroglycerin is often used sublingually to reverse attacks of acute angina.

Development of a controlled-release, long-acting nitroglycerin formulation, however, has been impeded mainly because of the pharmacokinetics and low vapor pressure of nitroglycerin. For example, attempts to solve these problems with oral or transdermal patch preparations has led to formulations which extend delivery of active drug for up to twenty four hours. A serious disadvantage associated with conventional extended delivery formulations, however, is that continually elevated levels of serum nitrates induce tolerance and reduced drug efficacy within a relatively short time.

The present invention, therefore, is directed to a controlled-release formulation which can be administered orally, once per day, causing therapeutic serum levels for about eighteen hours, thus effectively achieving anginal prophylaxis without induction of tolerance.

SUMMARY OF THE INVENTION

The present invention is directed to an organic nitrate formulation which, taken orally once per day, results in consistent therapeutically effective nitrate levels after the dose, without the development of tolerance, over a dosing period of at least one month. The organic nitrates preferred for purposes of the present invention are nitroglycerin, isosorbide 5-mononitrate and isosorbide dinitrate.

According to the invention, a controlled-release organic nitrate formulation for once-per-day oral administration is obtained by providing spheres having a core including at least one organic nitrate, and a membrane surrounding said core composed of a pharmaceutically acceptable, film forming polymer. The film forming polymer is effective to permit release of the at least one organic nitrate from the spheres, over a daily dosing period, at a rate that achieves a therapeutically effective level of the at least one organic nitrate, while effecting a drug holiday towards a latter portion of the daily dosing period so as not to induce tolerance.

Any organic nitrate within reason for treating a human mammal may be utilized in the formulation. Preferably, the organic nitrate is nitroglycerin, isosorbide 5-mononitrate, isosorbide dinitrate, or mixtures thereof. Furthermore, the organic nitrate may be in the form of a triturate with lactose and/or mannitol. For example, the nitroglycerin triturate can include 1-20 percent by weight nitroglycerin, the isosorbide 5-mononitrate triturate can include about 5-100 percent by weight isosorbide 5-mononitrate, and the isosorbide dinitrate triturate can include about 1 to 90 percent by weight isosorbide dinitrate.

The rate of release of the organic nitrate formulation may be described according to standardized dissolution testing procedures. In this regard, when the organic nitrate is nitroglycerin, the rate of release of the nitroglycerin from the formulation is substantially equivalent to a rate of release of the nitroglycerin as measured in vitro in a basket assembly according to U.S. Pharmacopoeia XXI, wherein less than 30% of the nitroglycerin is released after 1 hour of measurement, less than 40% of the nitroglycerin is released after 12 hours of measurement, and less than 90% of the nitroglycerin is released after 24 hours of measurement. When the organic nitrate is isosorbide 5-mononitrate triturate, the rate of release of the isosorbide 5-mononitrate is substantially equivalent to a rate of release of the isosorbide 5-mononitrate as measured in vitro according to dissolution testing in accordance with U.S. Pharmacopoeia XXI Apparatus II, paddle method, in a 7.5 pH phosphate buffer, wherein less than 30% of the isosorbide 5-mononitrate is released after 1 hour of measurement, less than 65% of the isosorbide 5-mononitrate is released after 4 hours of measurement, and less than 90% of the isosorbide 5-mononitrate is released after 12 hours of measurement. When the organic nitrate is isosorbide dinitrate, the rate of release of the isosorbide dinitrate is substantially equivalent to a rate of release of the isosorbide dinitrate as measured in vitro according to dissolution testing in accordance with U.S. Pharmacopoeia XXI Apparatus II, paddle method, in a 7.5 pH phosphate buffer, wherein less than 30% of the isosorbide dinitrate is released after 1 hour of measurement, less than 75% of the isosorbide dinitrate is released after 8 hours of measurement, and less than 100% of the isosorbide dinitrate is released after 16 hours of measurement.

In one embodiment of the invention, the core can be composed of a blend of at least one organic nitrate, a suitable carrier and a pharmaceutically acceptable application solution. Furthermore, the blend may also include a glidant, such as talc and/or silicon dioxide. The suitable carrier preferably comprises sugar spheres.

More specifically, the formulation of the present invention includes a blend of the organic nitrate triturate and glidants, such as talc or silicon dioxide, applied to sugar spheres using a pharmaceutically acceptable application solution, such as hydroxypropyl methylcellulose, ethylcellulose or other suitable cellulose derivatives, povidone, acrylic and methacrylic acid co-polymers, or pharmaceutical glaze in suitable solvents, such as water, ethanol, isopropyl alcohol, methylene chloride or mixtures and combinations thereof. In this regard, the organic nitrate triturate is applied to the sugar spheres along with the application solution.

The organic nitrate triturate and solution, in accordance with the present invention, is then applied to sugar spheres. The spheres or beads are dried at temperatures up to about 80° C. during which time the solvents are expelled. The spheres are then classified by size, and spheres of between 10 and 50 mesh may be selected and coated by means of a solution composed of ethylcellulose or acrylic and methacrylic acid esters or a pharmaceutical glaze in suitable solvents such as isopropanol, ethanol, methanol or methylene chloride, or mixtures thereof. This coating solution can contain one or more modifiers such as finely divided water-soluble particles, plasticizers or salts of fatty acids, water-insoluble finely divided particles or modifiers of pH. The spheres thus prepared are dried at temperatures up to about 80° C., and preferably within the range of about 25°–55° C., until the solvents are expelled and are then by themselves, or in a mixture of uncoated beads encapsulated in hard gelatin capsules or formed into tablets with standard equipment. Accordingly, the organic nitrate formulation in accordance with the present invention can be in the form of a capsule or tablet.

In another preferred embodiment of the invention, a seal coat may be positioned between the core and the membrane. The seal coat may be formed by coating the core with a solution comprising povidone in alcohol, talc, polyvinyl alcohol, hydroxypropyl methyl cellulose, cellulose derivatives, and mixtures of these materials.

The membrane according to the invention may comprise ethylcellulose, a methacrylic acid co-polymer, or a pharmaceutical glaze. The membrane may include plasticizers, such as diethyl sebacate, crotonic acid, diethyl phthalate, polyethylene glycol, citric acid esters, castor oil, and mixtures thereof. Furthermore, the membrane may include porosity modifier, such as talc and salts of fatty acids, e.g., calcium stearate. This membrane may be applied as a suspension comprising ethyl cellulose, propanetriol and sorbitol powder in a co-solvent, containing, by weight per volume, 5% ethylcellulose, 0.1% 1,2,3 propanetriol triacetate, and 1.7% sorbitol powder in a co-solvent system of about one part by volume methylene chloride and about two parts by volume isopropanol, or as a suspension containing ethylcellulose, diethyl phthalate, talc and calcium stearate in a co-solvent system of about one part by volume methylene chloride to about two parts by volume isopropanol.

The invention is also directed to a method of producing a controlled-release organic nitrate formulation for once-per-day oral administration including the steps of forming spheres containing at least one organic nitrate, and surrounding the spheres containing said at least one organic nitrate thereon with a membrane. The membrane is composed of a pharmaceutically acceptable, film forming polymer that is effective to permit release of said at least one organic nitrate from said spheres, over a daily dosing period, at a rate that achieves a therapeutically effective level of the organic nitrate, while effecting a drug holiday towards a latter portion of the daily dosing period so as not to induce tolerance.

More specifically, the organic nitrate triturate and application solution are applied to sugar spheres. The spheres or beads are dried at temperatures up to about 80° C. during which time the solvents are expelled. The spheres are then classified by size, and spheres of between 10 and 50 mesh may be selected. The membrane is then coated onto the spheres by coating the spheres with a solution composed of ethylcellulose or acrylic and methacrylic acid esters or a pharmaceutical glaze in suitable solvents such as isopropanol, ethanol, methanol or methylene chloride, or mixtures thereof. This coating solution can contain one or more modifiers such as finely divided water-soluble particles, plasticizers or salts of fatty acids, water-insoluble finely divided particles or modifiers of pH. The spheres thus prepared are dried at temperatures up to about 80° C., and preferably within the range of about 25°–55° C., until the solvents are expelled and are then by themselves, or in a mixture of uncoated beads encapsulated in hard gelatin capsules with standard equipment.

Additionally, the invention is directed to a method of treating mammals, including man, by the once-per-day oral administration of organic nitrate by orally administering once during each 24 hour time period a controlled-release organic nitrate formulation. This formulation is described above, and broadly is composed of spheres having a core including at least one organic nitrate, and a membrane surrounding said core composed of a pharmaceutically acceptable, film forming polymer, said film forming polymer being effective to permit release of said at least one organic nitrate from said spheres, over a daily dosing period, at a rate that achieves a therapeutically effective level of the organic nitrate, while effecting a drug holiday towards a latter portion of the daily dosing period so as not to induce tolerance.

The treating of the human mammal may be for the treatment of congestive heart failure, systemic hypertension, pulmonary hypertension, cardiomyopathic heart, valvular heart disease, vasospastic disease, congenital heart disease, or esophageal spasms. Relating to this, clinical studies have shown that the product is therapeutically efficacious, preventing or delaying the onset of chest pain for at least eighteen hours after a single daily dose.

BRIEF DESCRIPTION OF THE DRAWINGS

FIG. 1 illustrates a graph depicting the time to onset of chest pain after 28 days of dosing with the organic nitrate formulation described in Example 2.

FIG. 2 illustrates a graph depicting the effect on exercise tolerance before and after 28 days of dosing with the organic nitrate formulation described in Example 2.

DETAILED DESCRIPTION AND PREFERRED EMBODIMENTS

In accordance with the present invention, any organic nitrate suitable for use as a vasodilator, or otherwise appropriate for the treatment of cardiovascular disease, may be used. Preferred organic nitrates for purposes of the present invention are nitroglycerin, isosorbide 5-mononitrate and isosorbide dinitrate.

The organic nitrates are preferably used in the form of a triturate in lactose, mannitol or other suitable excipient. The term triturate as used herein means a powdered mixture of the organic nitrate and the foregoing excipient. The nitroglycerin is preferably from about 1-20 percent by weight of the triturate, and the isosorbide 5-mononitrate and isosorbide dinitrate are preferably about 5 to 100 percent by weight of the triturate.

The organic nitrate triturate is micronized and should be screened through a 200 mesh screen. Related to this a suitable glidant, such as silicon dioxide or talc, is preferably blended with the organic nitrate triturate to facilitate the handling of the raw material.

To aid in the deposition of the nitroglycerin blend on the nonpareils or sugar spheres, various materials including a pharmaceutical glaze, a solution of povidone in alcohol, a hydroxypropyl methylcellulose solution, a solution of methylcellulose or other cellulose derivatives may be used with a conventional coating pan or other equipment, such as CF Granulator, Merumerizer, Roto Granulator or the like. The size of the nonpareils preferably is within the range of 25 to 50 mesh.

Preferably, the above-prepared sugar spheres are coated with a seal coat in order to separate the active organic nitrate ingredient from the diffusion controlling polymeric membrane. Various materials may be utilized to form the seal coat, such as a 2%-25% povidone in isopropanol solution, talc, polyvinyl alcohol, hydroxypropyl methylcellulose, cellulose derivatives, and mixtures of these materials. Preferably, the weight of the seal coat per total weight of the organic nitrate containing sugar spheres is 2%-30% talc, 2%-25% polyvinyl alcohol, 2%-25% hydroxypropyl methylcellulose, or 2%-25% cellulose derivatives.

Onto the above-prepared sugar spheres is applied the pharmaceutically acceptable, film forming polymer membrane. Such polymeric membrane, which controls the diffusion of the organic nitrates, can be composed of ethylcellulose, a methacrylic acid co-polymer or a pharmaceutical glaze, as such, or may be modified with plasticizers, such as diethyl sebacate, crotonic acid, diethyl phthalate, polyethylene glycol, citric acid esters, and castor oil. Moreover, the polymeric membrane may include porosity modifiers, such as talc and/or salts of fatty acids, e.g., calcium stearate. The amount and nature of modifiers added to the polymeric membrane, as well as the thickness of the polymeric membrane, may be varied to achieve a desirable therapeutic effect.

The present invention is further illustrated by the following examples. All parts and percentages in the examples and throughout the specification and claims are by weight based on a total of 100%, unless otherwise indicated.

EXAMPLE 1

| Composition | Wt. Per Capsule |
| --- | --- |
| Nitroglycerin 10% Triturate | 250.0 mg |
| Silicon Dioxide | 7.0 mg |
| Sorbitol | 3.2 mg |
| Sugar Spheres | 29.5 mg |
| Ethylcellulose | 9.5 mg |
| 1,2,3 Propanetriol Triacetate | 1.0 mg |
| Talc | 52.6 mg |
| Povidone | 15.8 mg |

The nitroglycerin triturate is blended with the silicon dioxide and applied on the sugar spheres using 0.109 cc per capsule of a 10% povidone solution in isopropanol.

The so prepared beads are dried to remove the residual solvents at temperatures up to 80° C.

To these dried beads, an inert seal coat of talc with 0.0125 cc per capsule of a 13% povidone in isopropanol is applied. After the inert seal is applied, the beads are dried again to remove any residual solvents at varying temperatures up to 80° C.

To the above spheres the diffusion control membrane is applied. The membrane is applied as a suspension composed of 5% ethylcellulose with 0.1% 1,2,3 propanetriol triacetate, and 1.7% of sorbitol powder in a co-solvent system of one part methylene chloride and two parts isopropanol. The so prepared beads are dried to remove any residual solvents to temperatures up to 80° C.

The finished beads are tested for dissolution rates by the USP XXI apparatus I (basket) in pH 4.5 buffer and by the revolving bottle, with the following results.

| Dissolution Results Of Example 1 | | |
| --- | --- | --- |
| Time (h) | % Release USP Method | % Release Rev. Bottle |
| 1 | 5 | 8 |
| 12 | 20 | 22 |
| 24 | 70 | 71 |

EXAMPLE 2

| Composition | Wt. Per Capsule |
| --- | --- |
| Nitroglycerin 10% Triturate | 250.0 mg |
| Silicon Dioxide | 5.5 mg |
| Calcium Stearate | 37.1 mg |
| Ethylcellulose | 6.8 mg |
| Sugar Spheres | 34.7 mg |
| Diethyl phthalate | 0.1 mg |
| Talc | 65.6 mg |
| Povidone | 15.8 mg |

The nitroglycerin triturate is blended with the silicon dioxide and applied on the sugar spheres using 0.109 cc per capsule of a 13% povidone solution in isopropanol.

The so prepared beads are dried to remove the solvents at temperatures up to 80° C.

To these dried beads an inert seal coat of 30 mg of talc with 0.0125 cc per capsule of a 13% povidone solution in isopropanol is applied. After the inert seal is applied, the beads are dried again to remove any residual solvents at varying temperatures up to 80° C.

To the above spheres the diffusion control membrane is applied. The solution of this membrane is composed of 5% ethylcellulose with 0.1% diethyl phthalate in a co-solvent system composed of two parts of isopropanol and one part methylene chloride, applied with 35.6 mg of talc and the calcium stearate. The so prepared beads are dried to remove any residual solvents at temperatures up to 80° C.

The finished beads are subjected to the previously described testing methods.

| Dissolution Results - Example 2 | | |
|---|---|---|
| Time (h) | % Release USP Method | % Release Rev. Bottle |
| 1 | 7 | 9 |
| 12 | 22 | 23 |
| 24 | 67 | 65 |

As shown in FIGS. 1 and 2, the original drug dose maintains its effectiveness after twenty-eight days of daily therapy. Therefore, pharmacologic tolerance, observed in other formulations of long-acting nitrates and resulting in a requirement for increasingly higher doses of drug to obtain the same pharmacologic effect, does not occur with this formulation in this time period.

More particularly, the graph in FIG. 1 depicts 28 days of administration of optimum doses of the organic nitrate formulation according to the present example (KV/24 controlled-release nitroglycerin), and 28 days of placebo, crossing over in a randomly determined sequence. The dosing periods were separated by a 4-7 day washout. The 20 patients were subjected to treadmill testing before and at 12 hours, 16 hours, and 24 hours after the first and last daily doses in each period. In the treadmill test depicted in FIG. 1, the time to onset of chest pain is measured, and in the treadmill test depicted in FIG. 2, the ability to continue exercising, e.g., exercise tolerance, is measured.

As can be seen in FIGS. 1 and 2, efficacy of the organic nitrate formulation according to the instant example is superior to that of placebo at 12 and 16 hours after the daily dose, both on the first and last day of chronic dosing. Accordingly, based on these outcomes, one can conclude that the organic nitrate formulation of the instant invention is effective in helping angina patients lead more active lives with less limitations imposed by occurrences of severe chest pain, and that this benefit will be maintained over time without the need for continual dosage increases characteristic of known treatment formulations.

EXAMPLE 3

| Composition | Wt. Per Capsule |
|---|---|
| Nitroglycerin 10% | 500.0 mg |
| Silicon Dioxide | 7.0 mg |
| Sugar Spheres | 20.0 mg |
| Talc | 55.5 mg |
| Hydroxypropyl Methylcellulose | 23.4 mg |
| Pharmaceutical Glaze | 25.0 mg |
| Castor Oil | 1.8 mg |

The nitroglycerin triturate is blended with the silicon dioxide and fed into a CF Granulator while spraying with 211 mg per capsule of a 10% aqueous solution of hydroxypropyl methylcellulose.

The so prepared beads are dried to remove the solvent at temperatures up to 80° C.

To these dried beads is applied an inert seal coat of talc with 23.4 mg per capsule of a 10% aqueous solution of hydroxypropyl methylcellulose. After the inert seal is applied, the beads are dried again to remove any residual solvent at temperatures up to 80° C.

To the above spheres the diffusion control membrane is applied which is composed of a pharmaceutical glaze and castor oil.

The so prepared beads are dried to remove any residual solvent at temperatures up to 80° C.

The finished beads are subjected to the previously described testing methods.

| Dissolution Results - Example 2 | | |
|---|---|---|
| Time (h) | % Release USP Method | % Release Rev. Bottle |
| 1 | 10 | 15 |
| 12 | 26 | 26 |
| 24 | 72 | 79 |

EXAMPLE 4

| Composition | Wt. Per Capsule |
|---|---|
| Isosorbide 5-Mononitrate (50% Triturate) | 160.0 mg |
| Sugar Spheres | 61.0 mg |
| Talc | 46.0 mg |
| Povidone | 2.7 mg |
| Calcium Stearate | 8.6 mg |
| Pharmaceutical Glaze | 14.0 mg |
| Diethyl Phthalate | 0.2 mg |
| Ethylcellulose | 9.4 mg |

The isosorbide 5-mononitrate (IS-5-MN) triturate is applied on sugar spheres by means of 0.176 cc per capsule of the pharmaceutical glaze and the povidone solution.

The so prepared beads are dried to remove the solvents at temperatures up to 80° C.

To these dried beads an inert seal coat of talc is applied using 0.507 cc per capsule of polyvinyl chloride and pharmaceutical glaze. After the inert seal is applied, the beads are dried again to remove any residual solvents at varying temperatures up to 80° C.

To the above spheres, the diffusion control membrane is applied. The solution of this membrane is composed of 5% ethylcellulose, diethyl phthalate 0.1% in a co-solvent system composed of equal parts of isopropanol and methylene chloride, applied with talc and calcium stearate. The so prepared beads are dried to remove any residual solvents to temperatures up to 80° C.

The finished beads are subjected to a dissolution testing by the USP XXI Apparatus II (paddle) in a 7.5 pH phosphate buffer.

| Dissolution Results - Example 4 | |
|---|---|
| Time (h) | Found |
| 1 | 5% |
| 4 | 35% |
| 12 | 70% |

EXAMPLE 5

| Composition | Wt. |
|---|---|
| Isosorbide Dinitrate (Triturate) | 160.0 mg |
| Sugar Spheres | 117.0 mg |
| Talc | 31.0 mg |
| Povidone | 15.6 mg |
| Calcium Stearate | 2.9 mg |
| Ethylcellulose | 3.7 mg |

| Composition | Wt. |
| --- | --- |
| *-continued* | |
| Diethyl Phthalate | 0.1 mg |

The isosorbide dinitrate triturate is applied on sugar spheres by means of the povidone solution.

The so prepared beads are dried to remove the solvents at temperatures up to about 80° C.

To these dried beads an inert seal coat of talc is applied using essentially the same type of solutions as described above. After the inert seal is applied, the beads are dried again to remove any residual solvents at varying temperatures up to about 80° C.

The solution of this membrane is composed of 5% ethylcellulose and 0.1% diethyl phthalate in a solvent or solvent system composed of equal parts of isopropyl alcohol and methylene chloride, or isopropyl alcohol alone, applied with talc and calcium stearate. The so prepared beads are dried to remove any residual solvents at temperatures up to about 80° F.

The finished beads are subjected to a dissolution test by the USP XXI Apparatus II, (paddle), in a 7.5 pH phosphate buffer, with the following results:

| Dissolution Results - Example 5 | |
| --- | --- |
| Time (h) | Found |
| 1 | 6% |
| 8 | 51% |
| 16 | 85% |

From the foregoing description, one skilled in the art can easily ascertain the essential characteristics of the invention and, without departing from the spirit and scope thereof, can make various changes and modifications of the invention and adapt it to various usages and conditions.

What we claim is:

1. A method of treating a human with at least one organic nitrate without inducing nitrate tolerance, which comprises:
    administering a tablet or capsule containing at least one organic nitrate blended with nonpareils or sugar spheres, to the human over a 24 hour dosing period so as to achieve therapeutically effective levels of the at least one organic nitrate for at least about 16 hours, followed by less than therapeutically effective levels of the at least organic nitrate for the remainder of the 24 hour dosing period.

2. The method of claim 1, wherein the at least one organic nitrate is selected from the group consisting of nitroglycerin, isosorbide 5-mononitrate, isosorbide dinitrate, and mixtures thereof.

3. The method of claim 2, wherein the nitroglycerin comprises a nitroglycerin triturate.

4. The method of claim 3, wherein the nitroglycerin triturate includes a member selected from the group consisting of lactose, mannitol, and mixtures thereof.

5. The method of claim 3, wherein the nitroglycerin triturate includes 1 to 20% by weight nitroglycerin.

6. The method of claim 2, wherein the isosorbide 5-mononitrate comprises a isosorbide 5-mononitrate triturate.

7. The method of claim 6, wherein the isosorbide 5-mononitrate triturate includes a member selected from the group consisting of lactose, mannitol, and mixtures thereof.

8. The method of claim 6, wherein the isosorbide 5-mononitrate triturate includes about 5 to 100% by weight isosorbide 5-mononitrate.

9. The method of claim 2, wherein the isosorbide dinitrate comprises an isosorbide dinitrate triturate.

10. The method of claim 9, wherein the isosorbide dinitrate triturate includes a member selected from the group consisting of lactose, mannitol, and mixtures thereof.

11. The method of claim 10, wherein the isosorbide dinitrate triturate includes about 1 to 90% by weight isosorbide dinitrate.

12. The method of claim 1, wherein the human is treated for a condition selected from the group consisting of congestive heart failure, systemic hypertension, pulmonary hypertension, cardiomyopathic heart, valvular heart disease, vasospastic disease, congenital heart disease, and esophageal spasms.

13. The method of claim 1, wherein the at least one organic nitrate is administered to the human so as to achieve therapeutically effective levels of the at least one organic nitrate for about 18 hours, followed by less than therapeutically effective levels of the at least one organic nitrate for the remainder of the 24 hour dosing period.

14. A method of preventing the onset of nitrate tolerance in a human undergoing nitrate therapy, which comprises:
    administering a table or capsule containing at least one organic nitrate blended with nonpareils or sugar spheres, to the human over a 24 hour dosing period so as to achieve therapeutically effective levels of the at least one organic nitrate for at least about 16 hours, followed by less than therapeutically effective levels of the at least one organic nitrate for the remainder of the 24 hour dosing period.

15. A controlled-release pharmaceutical formulation for once-per-day oral administration, comprising spheres having a core including sugar spheres or nonpareils coated with at least one drug; a seal coat formed over the core; and a diffusion control membrane surrounding the seal coat comprising a pharmaceutically acceptable, film forming polymer, the film forming polymer being present in an amount effective to permit release of the at least one drug from the spheres, over a 24 hour dosing period, at a rate of release that achieves a therapeutically effective level of the at least one drug for at least 16 hours after administration of the pharmaceutical formulation, while providing less than therapeutically effective levels of the at least one drug for the remainder of the 24 hour dosing period so as not to induce tolerance in a patient administered the pharmaceutical formulation once every 24 hours.

16. A controlled-release pharmaceutical formulation for once-per-day oral administration, comprising sugar spheres or nonpareils having at least one drug; a seal coat formed over the core; and a diffusion control membrane surrounding the seal coat comprising a pharmaceutically acceptable film forming polymer, the film forming polymer being present in an amount effective to permit release of the at least one drug from the sugar spheres or nonpareils, over a 24 hour dosing period, at a rate of release that achieves a therapeutically effective level of the at least one drug for at least 16 hours after administration of the pharmaceutical formulation, while providing less than therapeutically effective levels of the at least one drug for the remainder of the 24 hour dosing period so as not to induce tolerance in a patient administered the pharmaceutical formulation once every 24 hours.

* * * * *

UNITED STATES PATENT AND TRADEMARK OFFICE
CERTIFICATE OF CORRECTION

PATENT NO. : 5,296,232
DATED : March 22, 1994
INVENTOR(S) : Paradissis, et. al.

It is certified that error appears in the above-indentified patent and that said Letters Patent is hereby corrected as shown below:

Claim 1, column 9, line 49, after "least" insert --one--.
Claim 6, column 9, line 63, change "a" to --an--.

Signed and Sealed this

Twenty-eighth Day of June, 1994

Attest:

BRUCE LEHMAN

Attesting Officer     Commissioner of Patents and Trademarks

Adverse Decision In Interference

Patent No. 5,296,232, George N. Paradissis, James A. Garegnani, Roy S. Whaley, ORAL ONCE- PER-DAY PHARMACEUTICAL FORMULATION WHICH DOES NOT INDUCE TOLERANCE, Interference No. 104, 617, final judgment adverse to the patentees rendered October 11, 2001, as to claims 1-16.
*(Official Gazette November 13, 2001)*